United States Patent [19]

Puscas et al.

[11] 4,216,207

[45] Aug. 5, 1980

[54] METHOD AND COMPOSITION FOR TREATMENT OF GASTRO-DUODENAL ULCERS

[75] Inventors: Ioan Puscas; Aurel Chiu; Livia Voicu, all of Simleul Silvaniei; Dorin Breazu, Cluj-Napoca; Iuliu Ciupe, Cluj-Napoca; Ioan Pop, Cluj-Napoca; Mioara R. Buten, Cluj-Napoca; Lazar Terec, Papiu Ilarion; Aurel Lerintiu, Simleul Silvaniei, all of Romania

[73] Assignee: Centrala Industriala de Medicamente Cosmetice Coloranti si Lacuri, Bucharest, Romania

[21] Appl. No.: 10,905

[22] Filed: Feb. 9, 1979

Related U.S. Application Data

[63] Continuation-in-part of Ser. No. 906,205, May 15, 1978, abandoned.

[30] Foreign Application Priority Data

May 14, 1977 [RO] Romania ............................... 90348

[51] Int. Cl.$^2$ ............................................. A61K 33/04
[52] U.S. Cl. ..................................................... 424/164
[58] Field of Search ...................................... 424/164, 4

[56] References Cited

U.S. PATENT DOCUMENTS 3,448,188  6/1969  Hookman ................................ 424/4

Primary Examiner—Frederick E. Waddell

[57] ABSTRACT

Gastro-duodenal ulcers may be effectively treated with a composition comprising a mixture of benzothiazole-2-sulfonamide to sulfate ranging from 1:1 to 1:3.

6 Claims, No Drawings

METHOD AND COMPOSITION FOR TREATMENT OF GASTRO-DUODENAL ULCERS

This application is a continuation-in-part of copending application, Ser. No. 906,205, filed May 15, 1978, now abandoned.

This invention relates to a medicinal composition. More particularly, the present invention relates to a composition suitable for use in the treatment of gastro-duodenal ulcers.

In the treatment of gastro-duodenal ulcers, both medical and surgical procedures have been commonly employed. Thus, for example, medicinal methods focusing upon the pathogenetic links which intervene in ulcerogenesis have included the neutralization of gastric acid secretions, dressing of gastric mucosa, the use of substances which enhance the factors protecting the gastric mucosa, anticholinergics (vagolitics), tranquilizers, and the like. Typical medications employed for these purposes are sodium bicarbonate, compositions including colloidal aluminum hydroxide, belladone extract, calcium, magnesium, bismuth salts, various silicates, scopolamine derivatives and combinations thereof with tranquilizers or flavoring substances which enhance ingestion.

The surgical procedures employed are directed to the elmination of those zones which play a role in the secretion of gastric acids. Typical of such procedures are gastric resection, antrectomy, vagatomy and variations thereof.

Although each of the foregoing techniques has been employed in the medical field with varying degrees of success, research efforts have continued with a view toward the development of improved medications, the prime focus being to obviate the necessity of surgery and its accompanying discomfort.

In accordance with the present invention, this end is attained by the use of a composition which is capable of inhibiting the carbonic anhydrase enzyme (carboanhydrase) which, when present in the renal tubules, erythrocytes, and other tissues, catalyzes the reversible hydration of carbon dioxide in accordance with the following equation:

$$CO_2 + H_2O \rightleftharpoons H^+ + HCO_3^-$$

During the course of this reaction, the liberated hydrogen ion is replaced by a sodium ion (Na+) of the tubal urine which then combines with the $HCO_3^-$ ion and, subsequently, reappears as sodium in the extra cellular fluid. The liberated hydrogen ion is eliminated either in the form of $NH_4^+$ ions or as an acid salt such as disodium phosphate. Inhibition of the enzyme pursuant to the invention results in diminution of carbon acid formation and contributes to the reduction in the rate of formation of hydrogen (H+) ions.

The composition employed in the practice of the present invention includes as its active constituent a mixture of benzothiazole-2-sulfonamide and barium sulfate, the ratio of sulfonamide to sulfate ranging from 1:1 to 1:3. For packaging purposes, the mixture is prepared in tablet form together with adjuvants commonly employed in effervescent tablets. It may, however, also be employed in powder form.

Studies have revealed that compositions described herein may be effectively employed in the treatment of gastro-duodenal ulcers in both children and adults, and is particularly effective in treating cases evidencing a chronic lesion, large niches, or those with an unusually high degree of gastric acid secretion. It may also be used to treat those with gastric evacuatory insufficiency.

Administration of the described medication may be effected orally, after meals, with a frequency ranging from 2-3 times per day over a time period ranging from 2-3 weeks or intermittantly over a 3 to 6 month period: Bed rest and diet are not required during the period of treatment.

The daily dosages required to attain the desired end range from 200-5000 mg of benzothiazole-2-sulfonamide, and from 200-10,000 mg of barium sulfate, specific dosages being based upon the body weight of the patient.

Typical of the compositions employed herein is one containing 33.33%, by weight, benzothiazole-2-sulfonamide and 66.67%, by weight, barium sulfate. It will be appreciated, however, that the sulfonamide may be employed in amounts ranging from 25-50 weight percent and the sulfate in an amount ranging from 75-50 weight percent.

Evaluation of patients treated with the composition containing 33.33% benzothiazole-2-sulfonamide, remainder barium sulfate, reveals that no diuresis occurs during the first 2 days of treatment nor is there any significant modification in urine or the pH of the blood.

Although the invention is described with reference to a specific embodiment thereof, it is to be expressly understood that it is in no way limited by the disclosure of such a single embodiment, but is to be construed within the context of the appended claims.

What is claimed is:

1. Pharmaceutical commposition for the treatment and healing of gastro-duodenal ulcers comprising a mixture of from 25-50 percent, by weight, benzothiazole-2-sulfonamide and from 75-50 percent, by weight, barium sulfate.

2. Composition in accordance with claim 1, wherein the ratio of sulfonamide to sulfate ranges from 1:1 to 1:3.

3. Composition in accordance with claim 1, comprising 33.33 percent, by weight, benzothiazole-2-sulfonamide, remainder barium sulfate.

4. Method for treatment of gastro-duodenal ulcers which comprises administering a pharmaceutical composition comprising from 25-50 percent, by weight, benzothiazole-2-sulfonamide and from 75-50 percent, by weight, barium sulfate to an ulcer patient, the daily dosage being such to supply from 200-5000 mg of sulfonamide and from 200-10,000 mg of sulfate based upon the body weight of the patient.

5. Method in accordance with claim 4, wherein the dosage is administered over a time period ranging from 2-3 weeks.

6. Method in accordance with claim 4, wherein the pharmaceutical composition is administered in tablet form.